United States Patent [19]

Pintucci

[11] Patent Number: 4,923,466
[45] Date of Patent: May 8, 1990

[54] KERATO-PROSTHESIS FOR TRANSCORNEAL IMPLANTATION AND PROCESS OF MANUFACTURE THEREOF

[76] Inventor: Stefano Pintucci, No. 37, Via Bertolini, 00197 Roma, Italy

[21] Appl. No.: 323,225

[22] Filed: Mar. 14, 1989

Related U.S. Application Data

[63] Continuation of Ser. No. 132,941, Dec. 9, 1987, abandoned.

[30] Foreign Application Priority Data

Dec. 15, 1986 [IT] Italy .................. 48744 A/86

[51] Int. Cl.$^5$ ............................ A61F 2/14; C09J 5/00
[52] U.S. Cl. ................................. 623/5; 623/901; 156/305
[58] Field of Search ........................ 623/4-6, 623/2, 11, 66, 901; 156/305

[56] References Cited

U.S. PATENT DOCUMENTS

| | | | |
|---|---|---|---|
| 3,436,763 | 4/1969 | Milauskas | 623/4 |
| 3,438,394 | 4/1969 | Nakib | 623/2 X |
| 3,752,162 | 8/1973 | Newash | 623/66 X |
| 4,080,709 | 3/1978 | Poler | 623/4 X |
| 4,129,470 | 12/1978 | Homsy | 623/66 X |
| 4,321,914 | 3/1982 | Begovac et al. | 623/66 X |
| 4,470,159 | 9/1984 | Peuman | 623/5 |

OTHER PUBLICATIONS

Visual Restoration with Plastic Corneal Implants by Frank M. Polack, Southern Medical Journal, vol. 65, No. 9, Sept. 1972, pp. 1118–1122.

Corneal Surgery (Book) by Louis J. Girard, Advanced Techniques in Ophthalmic Microsurgery, vol. Two, The C.V. Mosby Co., 1981, pp. 243–260.

*Primary Examiner*—Ronald L. Frinks
*Attorney, Agent, or Firm*—Mason, Fenwick & Lawrence

[57] ABSTRACT

A kerato-prosthesis for transcorneal implantation which comprises an optical part consisting of a biocompatible clear material in the shape of a small cylindrical frustum, and a supporting haptic part in the shape of a small disk which is drilled at the center and is made up of an alloplastic, biocompatible, synthetic, porous or of the closed cell type, which cannot be reabsorbed and is capable of allowing the growth of human tissues inside, both parts being connected to each other respectively at the points corresponding to a portion of the lateral surface of said small cylinder and of the inner peripheral edge of said hole, and a process for manufacturing said kerato-prosthesis.

9 Claims, 1 Drawing Sheet

KERATO-PROSTHESIS FOR TRANSCORNEAL IMPLANTATION AND PROCESS OF MANUFACTURE THEREOF

This application is a continuation, of application Ser. No. 132,941, filed 12/9/87, now abandoned.

The present invention relates to a kerato-prosthesis for transcorneal implantations and to a process for manufacturing the same as well.

More particularly, this invention relates to a prosthesis for the cornea to be employed in all cases wherein the same has lost its clearness as a result of contact with caustic compounds, mechanical stresses, scalds, destruction of the anterior segment of the eye due to traumata or to diseases such as eye pemfighoid, Steven-Johnson's syndrome, in which the conditions of the eye do not make possible to perform a cornea grafting.

Kerato-prostheses, which normally are made upof an "optical" part and of a part for anchoring to the optical part of the eye, which part is called "haptic", make use at present, as regards the optical part, almost constantly of a polymethylmethacrylate (PMMA) cylinder, whereas they differe remarkably as regards the haptic part, as well as regards the choice of the materials employed for fastening the same to the eyeball, as shown in table 1 which follows and reports some fundamental solutions:

TABLE 1

| Materials employed for the haptic part | Materials employed for covering the haptic part |
| --- | --- |
| Cardona (1983): A TEFLON disk bearing some holes | A DACRON net + periosteum (or "fascia lata") + conjunctiva. In case of retraction of conjunctival fornices, covering with the upper eyelid. |
| Girald (1983): A DACRON net | Front: Tenone's capsules + conjunctiva<br>Back: PMMA nut and bolt<br>In cases as above, covering with upper eyelid or with labial mucosa |
| Polack (1983): A ceramic disk bearing holes | Periosteum (or "fascia lata") + Tenone's capsule + conjunctiva. In cases as above, covering only with the skin of the upper eyelid |
| Choyce (1977): A Perspex disk bearing holes | A corneal edge (0–9.0–10 mm) bearing a hole for allowing the optical part to pass + a corneal-scleral lamellar edge (0–13 mm) which is opened at the center after 4–6 weeks. | and in addition Krasnov (1985) for strengthening the cornea employs an autologous cartilage.

The differences in the procedures and in materials employed by each of the Authors previously cited are due to the search for a material capable of favoring the adhesion between the haptic part of kerato-prostheses and the ocular tissues in a stable way, by mechanical means and without a time term.

The main complication with all such kerato-prostheses consists in the expulsion (about 25%) of the same caused by the tendency of the organism to expell or to include any foreign body implanted in the same, especially when such foreign body is present partly within the organism and partly outside it (mesoprosthesis) as is the case with keratoprostheses.

According to Dohlman, the cause of such complication is due to the action on the corneal stroma and on the tissues which support the prosthesis, of proteolytic enzymes such as collagenases liberated in the lachrymal film by polymorphonucleate leucocytes and by all elements intervening in the inflammation. The validity of Dohlman's theory seems to be confirmed by the preventive action of collagenase inhibitors (acetylcysteine, immunosuppressors), as well as by the therapeutical contact lenses and by cyanoacrylic adhesives which prevent the tissues from contacting the enzymes.

Cardona observes that tissue alterations begin around the optical part and they are favored by the motion of the eyelids. Once the softening of the cicatrice tissue which supports the keratoprosthesis has begun, the following drawbacks occur:

(1) leakage of aqueous humour
(2) hypotonicity
(3) infections
(4) formation of membranes on the back of the prosthesis
(5) extrusion of the prosthesis (within 1–3 months).

In an attempt at removing the drawbacks mentioned above and mainly aiming at integrating the keratoprosthesis with the tissues around the same, Prof. Strampelli employs for the haptic part the patient's tisses by surgically drawing an osseous-alveolar lamina and a dentine lamina from a monocusp tooth together with the alveolar dentary ligament which joins the same (odontokeratoprosthesis). After drilling the laminae and fastening of the small PMMA lens to the dental part by means of an acrylic resin, the prosthesis is implanted for about two months into the thickness of the lower eyelid in order to obtain sterility and to cause the cicatrice tissue to take root in the osseous surface, which cicatrice tissue is needed for fastening the prosthesis to the eyeball by means of sutures.

The eyeball is prepared by implantation of a wide and thick margin of the labial mucosa on the cornea and on the sclera all around, by previously removing the corneal epithelium, peritonia and recession of the eyeball till the insertion of the straight muscles.

After three months, with a repeated operation, the labial mucosa is detached, the cornea is drilled and the prosthesis is implanted and fastened by means of sutures to the eyeball, then the labial mucosa is drilled for allowing the optical part to pass through the same and finally the labial mucosa is sutured.

Such procedure, which is called "odontokeratoprosthesis," has the advantage of employing some physiological characteristics of teeth. The epithelium of the gums does not expell teeth because it fails to coat the alveolus occupied by the alveolar cement and by the connectival fibers. However, some drawbacks affect this technique as necrosis of the osseous-dental tissue, can occur during working also as a result of mechanical stresses, and also toxic effects can occur due to the liberation of monomers during polymerization of the acrylic adhesive, as well as phlogosis from mechanical stresses between the osseous tissue which is rigid and the sclerocorneal-oral mucosa which is elastic, the absence of metabolic exchanges between the back face of the haptic part (dentine) and the cornea, which is due to the lack of biological integration between the two surfaces, necrotic phenomena and inflammation phenomena with osseous reabsorption and the loss of the prosthesis, as occurs in dental reimplantations. Moreover, said odontokeratoprosthesis can hardly be implanted from the surgical viewpoint and it asks of the patient the loss of a tooth and numerous surgical operations.

As to the alloplastic materials to be employed in the construction of keratoprostheses, it is to be mainly observed that:

(a) the hole-bearing disks of PMMA employed by Choyce for the haptic part and those of TEFLON employed by Cardona do not become integrated with the ocular tissues because they lack the necessary porosity for the growth or colonization of said tissues; the cicatrice tissue around such disks has few small diameter vessels so that it has a tendency to necrosis and retraction.

(b) Ceramics formed by aluminum oxide crystal aggregates ($Al_2O_3$ or corundum) are rigid and hard, and they have no pores and they can be worked into polished or rough surfaces to obtain the optical part and the haptic part of keratoprostheses.

(c) Ceramics in orthopaedic surgery and in densitry do not cause complications because they have a good biocompatibility and they are implanted in a rigid tissue which is not subject to deformations; when they are employed in keratoprostheses, they cause a deformation of the implantation bed because of their rigidity and they not follow the deformation arising during ocular motion and caused by the presence of fingers; in addition, keratoprostheses realized with ceramic materials, as well as those consisting of PMMA and polytetrafluoethylene, such as that marketed under the trademark TEFLON and terephtalatous polyethylene such as marked under the trademark DACRON, do not become integrated with ocular tissues with which they develop a poor adhesion and around which just a single fibrous tissue forms.

In order to remove all drawbacks mentioned above, it is necessary that the haptic part of the keratoprosthesis be of deformation and elastic characteristics similar to those of the ocular tissues for distributing uniformly the mechanical stresses on the same without damaging them. The haptic part in addition is to be made up of materials which, in addition to be biocompatible, also become an integrated part of the osseous tissue in order to allow the cellular and extracellular exchanges of catabolites, of exudates, of oozing, of oxygen, etc. to occur between the tissues around the prosthesis.

It is to be remarked that mesoprostheses are implanted in contact with connectival and epithelial tissues whose continuity is thus interrupted. As the contact inhibition is lacking, the epithelium proliferates and covers the outer surface of the mesoprosthesis so transforming the same into an endoprosthesis or it coats the inner surface with formation of membranes at the back of the prosthesis, which membrane cause the extrusion of the prosthesis itself.

In order the epithelium can include a prosthesis or can extrude the same, it is necessary that some particular biological conditions occurs such as the lack of contact inhibition of epithelium and mechanical conditions such as the presence of a space to be coated between the prosthesis and the tissues around the same. This happens when the haptic part is not integrated with the ocular tissues but it is joined to the same by a cicatrice tissue which as a tendency to natural retraction and to necrosis following mechanical stresses, decubitus or phlogosis. In order to avoid the extrusion of the prosthesis the haptic part is to become an integrated part with the tisues around the same and to form a living tissue, free from any discontinuities up to the optical part as will be suggested according to the present invention.

Indeed, to that aim the present invention suggests the use, for the haptic part, of synthetic materials which are porous or anyway provided with inner spaces (closed cells) which allow the growth of human tissues in their inside part (colonizazion) to occur and in addition are not re-absorbable, and are biocompatible and alloplastic.

Preferably, fabrics are employed which are made up of DACRON or TEFLON fibers, of polytetrafluoroethylene fibers as for instance GORE-TEX, (expanded polytetrafluoroethylene) and polymers reinforced with carbon fiber or PROPLAST.

More precisely, as regards DACRON, this is the well-known felt employed in heart surgery because it is endowed with the following characteristics:
the absence of necrosis and decubitus
the absence of rejection
the absence of reabsorption
the absence of allergic reactions
time stability
workability as regards sizes and shapes
easy sterilization
biological and mechanical integration with the colonizing tissues;
the availability of cellular and intercellular exchanges within the living tissues colonizing the prostheses;
the absence of cicatrice retraction.

The optical part can be adequately realized with biocompatible transparent materials such as for instance advantageously polymethylmethacrylate (PMMA), polyethylmethacrylate (PEMA), the bioglass (silicone oxide, calcium, sodium and phosphorus), and corundum (aluminum oxide), and so on.

Moreover, in order to realize a suitable keratoprosthesis for the aims mentioned above, it is necessary that the fastening of the optical part with the haptic part do not alter the biocompatibility of keratoprosthesis and to that aim such fastening is obtained according to the present invention employing PMMA or PEMA dissolved in a specific solvent or anyway in the liquid state. The PMMA in the liquid state combines chemically with the optical part and mechanically, through infiltration, with the DACRON fabric.

Preferably solvents are employed such as dichloroethylene and acetone which are capable of making the optical part temporarily liquid so as to allow the infiltraton to occur and next the penetration of the optical part with the haptic part, so realizing a complete adhesion of the two parts once the solvent is evaporated.

It is interesting to note that the prosthesis according to the present invention does not ask for mechanical working on living tissues, as occurs for instance in odontokeratoprosthesis and to note that the materials said prosthesis is made up of are polymerized and sterilized before the implantation.

In addition, advantageously said prosthesis adapts itself mechanically during the surgical operation to the implantation bed, due to the flexibility of the DACRON felt which in turn, when is implanted, becomes histologically integrated with the anterior and posterior connectival tissues around the same and by which tissues it becomes integrally colonized with the formation of a connectively continuous and uniformly vascularized tissue allowing the intracellular and extracellular exchanges necessary to its metabolism to occur; as such prosthesis has no empty parts (holes) and as it becomes completely penetrated by living tissues, it does not allow the passage of epithelium along the small length in the sense from the front to the back part because it gives rise to a living connectival structure.

In conclusion the essential feature of the present invention consists in the selection of particular synthetic materials, for instance PMMA for the optical part in association with material such as DACRON for the haptic part which parts are bonded to each other by means of the fasteing technology mentioned above.

Accordingly, it is a specific object of the present invention a keratoprosthesis for transcorneal implantations, characterized in that it comprises an optical part made up of a clear biocompatible material in the shape of a small cylindrical frustum, a supporting haptic part in the shape of a small disk bearing a hole in the center, said disk being of a synthetic material, which is porous or of the closed cell type, biocompatible, alloplastic and which cannot be reabsorbed, and is capable of allowing the growth of human tissue in its inside part to occur, said parts being connected to each other at the points corresponding respectively to a portion of the lateral surface of said small cylinder and of the inner peripheral edge of said hole.

Preferably said transparente biocompatible material making up the optical part of the prosthesis is polymethylmethacrylate.

According to another embodiment of the present invention, the compounds advantageously employed are bioglass (silicone oxide, calcium, sodium, phosphorus), corundum (aluminum oxide) or silicone.

As for the synthetic materials which the haptic part is made up of, the present invention suggests preferably fabrics consisting of DACRON or TEFLON fibers.

Alternatively, polytetrafluoroethylene fabrics can be advantageously employed, as for instance GORE-TEX or fabrics made up of polymers reinforced with carbon fibers or PROPLAST.

As for the structural sizes of said optical part, it has a length between 1.5 and 20 mm and a diameter between 1.5 and 10 mm, and said haptic part has a thickness between 0.10 and 2.5 mm and a diameter between 2 and 20 mm.

Keratoprosthesis for transcorneal implantation according to the present invention is realized preferably through a process which provides the fastening of the optical part to the haptic part characterized in that it comprises the operation of dissolving temporarily and partially the optical part by means of a solvent in which a polymeric material has been possibly dissolved, of causing the portion of optical part so temporarily dissolved to penetrate the haptic structure at a limited thickness zone in its outer peripheral edge till penetrating the same fully, and of evaporating the solvent till obtaining a stable mechanical bond between the two parts following the evaporation of the solvent, and finally of sterilizing the prosthesis.

As already mentioned above, dichloroethylene or acetone $(CO(CH_3)_2)$ are preferably employed as the solvent, while polymethylmethacrylate or polyethylmethacrylate are preferably employed as the polymeric material to be dissolved in the solvent.

Preferably the sterilization is carried out after eliminating by boiling in distilled water any trace of the monomer and of working scraps employing gaseous ethylene oxide which is absorbed by the polymeric material (PMMA and PEMA) by 2% by weight and subjecting successively the piece so obtained overnight to a negative pressure of $10^{-3}$ mm Hg or otherwise allowing the same to rest for days before implantation.

It is to be remarked that both the front surface and the back surface of the optical part can be subjected to optical working according to the optical anatomical and physiological needs of the patient.

Moreover, the optical part can be worked on its inner surfaces to form a compound optics or it can be formed by different optical surfaces of different refractive indices.

In case the outer surface of the optical part does not serve to the passage of light, it can be opaque or painted.

The keratoprosthesis according to the present invention is intended for practical application in patients belonging to two classes: those having "dry eyes" and heavy alterations as regards their conjunctivas, who must be subjected to transpalperbral implantation and those who do not show such alterations and can be subjected to a surgical operation adopting the technique which provides the covering of the prosthesis with oral mucosa.

In practice, it has been observed in the case of implantantations performed in a group of five patients that, respectively 18, 12, 9, 8, 7, 5 months after the operation all patients showed a very good sight and they did not undergo further complications.

The present invention will be disclosed in the following with particular reference to a preferred embodiment of the same which is illustrated in the enclosed drawings wherein.

Figure 1:
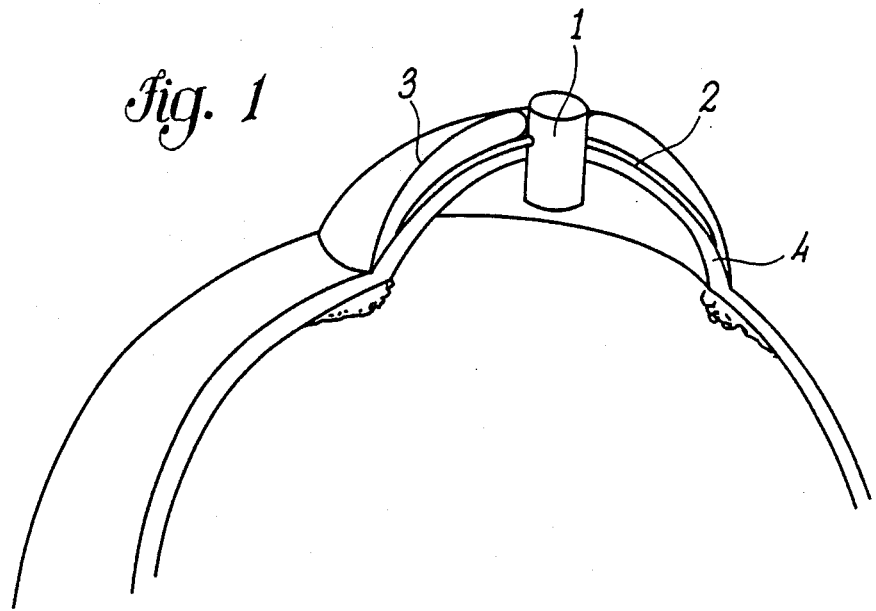
FIG. 1 shows a perspective section view of a device according to the present invention as applied to the eye.

FIG. 1 shows that the device of the present invention is made up of a small clear cylinder 1 which is fastened at the points corresponding to a peripheral zone along the lateral surface to the circular portion of DACRON fabric 2 which is drilled at its center and is applied to the central part of the ocular body through an opening obtained in the palpebral tissue 3 and in the scleral tissue 4.

Figure 2:
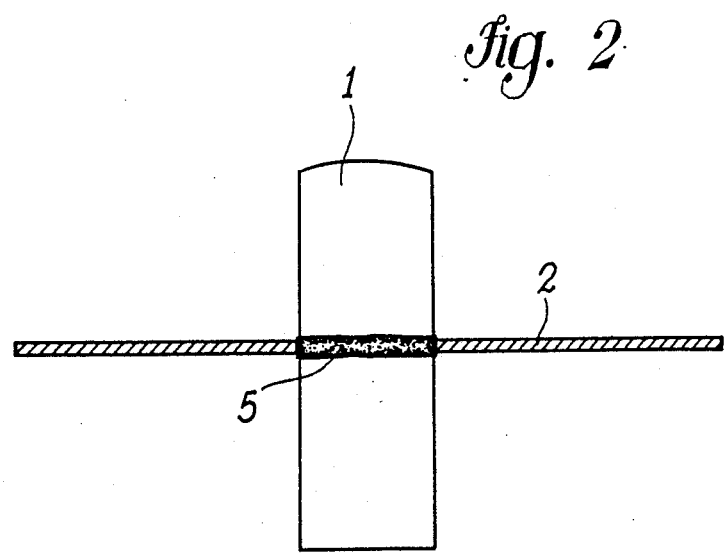
FIG. 2 shows a vertical section view of the device.

FIG. 2 shows more clearly the fastening zone 5 between the transparent body 1 and the DACRON fabric 2. As already explained above, the fastening operation has occurred all along said zone following the dissolution of the synthetic transparent material which member 1 is made up of and following the adhesion between the inner peripheral edge of the hole in the fabric 2 and the outer surface of member 1.

The present invention has been disclosed just for illustrative and not for limitative purposes with reference to some preferred embodiments of the same but it is to be understood that modifications and changes can be introduced in the same by those who are skilled in the art without departing from the spirit and scope of the invention for which a priority right is claimed.

I claim:

1. A keratoprosthesis for transcorneal implantations, characterized in that it comprises an optical part comprising a biocompatible transparent material in the form of a small cylindrical body, a one piece supporting haptic part comprising a synthetic material having inner spaces that is biocompatible alloplastic and which cannot be reabsorbed, and in addition allows human tissues to grow within said haptic part, having the shape of a small disk which is drilled at its center to form a hole, said optical part and said haptic part being directly fixedly bonded to each other at the points corresponding to a portion of the lateral surface of said small cylinder and of the inner peripheral edge of said hole.

2. A keratoprosthesis for transcorneal implantations according to claim 1, wherein said synthetic material is porous.

3. A keratoprosthesis for transcorneal implantations according to claim 1, wherein said synthetic material is of the closed cell type.

4. A keratoprosthesis for transcorneal implantations according to claim 1, wherein said optical part is connected to said haptic part by a dissolved portion of said optical part, said portion having penetrated said haptic part by infiltration to obtain a stable bond between said optical part and said haptic part.

5. A keratoprosthesis for transcorneal implantations according to claim 1, wherein said haptic part is a felt of terephtalatous polyethylene.

6. A process for the manufacture of a keratoprosthesis for transcorneal implantations, said process comprising the operation of fastening the optical part to the haptic part, and being characterized in that it comprises the operations of dissolving temporarily and partially the optical part by means of a solvent in which a polymeric material has been dissolved, of causing the porton of the optical part that has been temporarily dissolved to penetrate by infiltration the haptic structure till penetrating fully the same within a zone of thickness limited to its outer peripheral edge, of causing the solvent to evaporate till obtaining a stable mechanical bond between the two parts following the evaporation of the solvent, and finally of sterilizing the prosthesis.

7. A process for the manufacture of a keratoprosthesis for transcorneal implantations according to claim 6 wherein said solvent is dichloroethylene or acetone.

8. A process for the manufacture of a keratoprosthesis for transcorneal implantations according to claim 6, wherein said polymeric materials to be dissolved in the solvent is polymethylmethacrylate or polyethylmethacrylate.

9. A process for the manufacture of keratoprosthesis for transcorneal implantations according to claim 6, wherein sterilization is carried out after removing by boiling in distilled water all traces of the monomer and of working scraps, employing gaseous ethylene oxide which is absorbed by the polymeric material (PMMA and PEMA) by 25% by weight and next subjecting the piece so obtained overnight to a negative pressure of $10^{-3}$ mm Hg or allowing the same to rest for at least one day before performing the implantation.

* * * * *